United States Patent [19]

Krishnamurti et al.

[11] Patent Number: 5,144,076
[45] Date of Patent: Sep. 1, 1992

[54] PREPARATION OF 3,5-DIAMINO BENZOTRIFLUORIDE

[75] Inventors: Ramesh Krishnamurti, Amherst; Lawrence B. Fertel, Williamsville; Henry C. Lin, Grand Island, all of N.Y.; Mahendra K. Dosi, Alpharetta, Ga.

[73] Assignee: Occidental Chemical Corporation, Niagara Falls, N.Y.

[21] Appl. No.: 769,910

[22] Filed: Oct. 1, 1991

Related U.S. Application Data

[63] Continuation-in-part of Ser. No. 608,912, Nov. 5, 1990, abandoned.

[51] Int. Cl.$^5$ ............................................ C07C 209/36
[52] U.S. Cl. ..................................... 564/417; 564/404; 564/405; 564/407; 564/406; 564/422; 564/423
[58] Field of Search .............. 564/406, 404, 405, 407, 564/417, 422, 423

[56] References Cited

U.S. PATENT DOCUMENTS 4,022,795  5/1977  Bamfield et al. .................... 564/417

FOREIGN PATENT DOCUMENTS 38465  10/1981  European Pat. Off. .

OTHER PUBLICATIONS

Weizmann, American Chemical Society, vol. 71, Dec. 1949, pp. 4154–4155.

*Primary Examiner*—Richard L. Raymond
*Assistant Examiner*—Shailendra Kumar
*Attorney, Agent, or Firm*—Richard D. Fuerle

[57] ABSTRACT

3,5-Diaminobenzotrifluoride can be produced, in a single step, by reacting 4-chloro-3,5-dinitro benzotrifluoride in a suitable solvent, with hydrogen gas, in the presence of a catalyst comprising palladium on a suitable carrier, and in the presence of a suitable base.

20 Claims, No Drawings

PREPARATION OF 3,5-DIAMINO BENZOTRIFLUORIDE

This application is a CIP of 07/608,912, Nov. 05, 1990, now abandoned.

BACKGROUND OF THE INVENTION

This invention relates to a process for the preparation of 3,5-diaminobenzotrifluoride by the reduction of 4-chloro-3,5-dinitrobenzotrifluoride using hydrogen as a reducing agent in the presence of palladium on charcoal as a catalyst. 3,5-Diaminobenzotrifluoride is a valuable intermediate for use in the synthesis of polyimide polymers.

The reduction of aromatic nitro compounds containing halogen on the aromatic ring is unpredictable. Hydrogenation using a palladium on charcoal catalyst generally reduces the nitro group to an amine. However, the hydrogenation has been reported to fail in some cases. In addition, the effects of such hydrogenation upon a ring halogen are unpredictable. Occasionally the ring halogen is removed from the ring and replaced by a hydrogen. However, in many cases the hydrogenation leaves the ring halogen intact.

A. Weizmann discloses in J. Am. Chem. Soc., 71, 4154 (1949), that the catalytic hydrogenation of diethylaminoethyl-4-nitro-2-chlorobenzoate using palladium on barium sulfate as a catalyst was impractical from a preparative point of view. The nitro compound was often incompletely reduced. The chlorine was occasionally removed from the ring while in other reactions it remained on the ring. Similar hydrogenation experiments conducted with 2-chloro-4-nitrobenzoic acid and its ethyl ester, using palladium on barium sulfate as a catalyst, produced variable results depending upon the solvent employed. In ethyl acetate, the reduction proceeded with retention of the chlorine, and the acid and the ethyl ester gave quantitative yields of 4-amino-2-chlorobenzoic acid and ethyl 4-amino-2-chlorobenzoate, respectively. In other words, the use of ethyl acetate as a solvent caused reduction without removal of the chlorine attached to the ring. In isopropyl alcohol, the 2-chloro-4-nitrobenzoic acid and its ethyl ester were reduced to 4-aminobenzoic acid and its ethyl ester respectively. In other words, the chlorine was lost in the reduction process. An aqueous solution of sodium 2-chloro-4-nitrobenzoate yielded, on workup, 4-aminobenzoic acid.

Bouchet et al. disclose in Syn. Commun., 4, 57-9 1974) that para-nitrochlorobenzene may be reduced to para-chloroaniline using hydrogen in the presence of a palladium on carbon catalyst.

Ovchinnikov, et al. (in Z. Prikl. Khim., (62), 37-44 (1969)) that meta- and para-chloronitrobenzenes may be hydrogenated to meta- and para-chloroanilines respectively using hydrogen gas and a 2% palladium on carbon catalyst. Approximately 2% dehalogenation was observed. It was also observed that the amount of dehalogenation was related to the type of carbon used as the catalyst carrier as well as the height of the catalyst bed.

U.S. Pat. No. 4,022,795 discloses a process for dehalogenating aromatic compounds using a formic acid salt and a hydrogenation catalyst. If a nitro group is present in the aromatic molecule, it may be reduced in the process. Under certain conditions, internuclear bonds are formed and thus, a chlorobenzene may yield a biphenyl derivative.

U.S. Pat. No. 3,666,813 discloses that aromatic haloamines may be prepared by hydrogenating the corresponding chloro-nitro aromatic compound in the presence of a modified palladium on charcoal catalyst. The palladium on carbon catalyst is modified by treating it with a solution of a bismuth, lead or silver salt.

European Pat. Application EP 88667 (as abstracted in Chem. Abstracts 100:52475m and Derwent accession #C83-089930) discloses that chlorinated or brominated methylenedianilines may be prepared by the nitration and reduction of the corresponding aromatic halides. The reduction is carried out in methanol solvent with hydrogen gas in the presence of 5% palladium on carbon as a catalyst. The halogen is not removed in this process.

European Pat. Application EP-38465 teaches the reduction of 2-trifluoromethyl-4-chloronitrobenzene to 2-trifluoromethylaniline in a single step using hydrogen gas in a polar medium. The preferred solvent is water and/or a 1-3 carbon alcohol, especially methanol, and the preferred bases are alkali hydroxides, ammonia, or lower aliphatic amines.

Chakrabarti et al. disclose in two papers (J. Med. Chem. 23, p. 878 and 884 (1980)) a multi-step reduction reaction in which the first step is hydrogenation using 10% palladium on carbon as a catalyst. The molecules that are subjected to hydrogenation are substituted nitrobenzenes with a halogen at the 3-position and a substituted amino group at the 6-position. In one paper the compound studied has fluorine as the halogen and in the other the halogen is chlorine. In each case, the nitro group was reduced to the amine while the halogen was not attacked.

Japanese Pat. No. 63/010739 (as abstracted in Chem. Abstracts 109:92449y) discloses that chloro-fluoro-benzotrifluoride derivatives can be dechlorinated using hydrogen gas and 5% palladium charcoal catalysts in a methanol solvent. The ring chlorines are preferentially removed over the ring fluorines.

Vergnani et al. disclose in Helv. Chim. Acta, 68, 1828, (1985), that 5-bromo-2-methyl-8-nitro-1,2,3,4-tetrahydroisoquinoline undergoes simultaneous removal of the aromatic bromine and reduction of the nitro group to an amine when treated with hydrogen gas in the presence of a 10% palladium on charcoal catalyst, triethyl amine and methanol as a solvent.

Japanese Pat. No. 58157749 (as abstracted in Chem. Abstracts 100:51247b) discloses that 2,2',4-trichloro-4',5-dinitrodiphenyl ether may be hydrogenated in the presence of 5% palladium on carbon catalyst in methanol to form 5 3,4'-diaminodiphenyl ether.

Crampton and Greenhalgh have disclosed, in J. Chem. Soc., Perkin Transaction II, p. 187 (1986), that 4-chloro-3,5-dinitrobenzotrifluoride is subject to nucleophilic attack at the carbon-chlorine bond. Thus, hydroxide ion can displace the chlorine to yield 4-hydroxy-3,5-dinitro benzotrifluoride. The substance that is reduced using the process of this invention, that is, 4-chloro-3,5-dinitro benzotrifluoride, is a rather reactive molecule and can undergo side reactions during any reduction process.

Attempts were made in our laboratories to reduce 4-chloro-3,5-dinitro benzotrifluoride using sodium formate and a palladium on carbon catalyst. A variety of dipolar aprotic solvents and methanol were used. In all cases the reduction was either incomplete or did not occur at all, and the products formed indicated that the 4-chloro group had been displaced to form either 4-hydroxy compounds or, in the case of methanol, a 4-methoxy compound. (See Comparative Examples 1-4.) Attempts were also made to use sodium formate as a base. The reaction product was a mixture of the desired 3,5-diaminobenzotrifluoride and the undesirable 4-chloro-3,5-diaminobenzotrifluoride. (See Comparative Example 8)

SUMMARY OF THE INVENTION

Surprisingly, we have now found that 3,5-dinitro benzotrifluoride can be produced, in a single step, by reacting 4-chloro-3,5-diamino benzotrifluoride, in a suitable solvent, with hydrogen gas, in the presence of a catalyst comprising palladium on a suitable carrier in the presence of a suitable base. The nature of the base and solvent are crucial in the present invention. The present process is advantageous in that the starting material, 4-chloro-3,5-dinitrobenzotrifluoride is commercially available.

DETAILED DESCRIPTION OF THE INVENTION 3,5-Dinitro benzotrifluoride can be produced, in a single step, by reacting 4-chloro-3,5-diamino benzotrifluoride, in a suitable solvent, with hydrogen gas, in the presence of a catalyst comprising palladium on a suitable carrier, and in the presence of a suitable base. The reaction is conducted at moderate pressure; that is, about 50 to 300 psig. At the lower end, the pressure is not critical. Although the reaction can be run at pressures less than 50 psig, such reactions tend to be slow. Accordingly, it is preferred to run the reaction at about 50 psig or above. A hydrogen pressure of 300 psig is not an upper limit on the useable pressure, but is rather the upper end of the preferred region of operation.

The reaction can be conducted at moderate temperatures between room temperature and about 100° C. If the reaction is run at a temperature much lower than room temperature, it tends to be too slow to be useful. On the other hand, at temperatures above 100° C., high molecular weight side products are formed.

Selection of the solvent is important in conducting this reaction. Nucleophilic solvents are not suitable for this process since they can attack the halogen and lead to unwanted side products. A particular example of this is methanol which can displace the chlorine and lead to the 4-methoxy compound as a product. This problem is illustrated in Comparative Example 4. Other primary alcohols are also unsuitable solvents.

Dipolar aprotic solvents, such as dimethyl formamide, N-methyl-2-pyrrolidone, and dimethyl sulfoxide, are not suitable solvents because their use tends to lead to the formation of hydroxy derivatives. This is illustrated in Comparative Examples 1-3.

C3 to C6 secondary and tertiary alcohols, which are larger molecules than methanol, are suitable solvents because they cannot readily attack the somewhat sterically hindered 4-chloro group. Other suitable solvents include acetonitrile, ethers such as diethyl ether, tetrahydrofuran, ethylene glycol dimethyl ether (glyme), diethylene glycol dimethy ether (diglyme), triethylene glycol dimethyl ether (triglyme), and tetraethylene glycol dimethyl ether (tetraglyme), and low molecular weight esters obtained from C2 to C4 acids with C2 to C4 alcohols such as ethyl acetate, isopropyl acetate, n-propyl acetate, butyl acetates, ethyl propionate, and ethyl butyrate. The most suitable solvent is ethyl acetate.

The reaction tends to be rather slow in the absence of a base. The slowness is illustrated in Comparative Examples 5-7. Although we do not wish to be bound by theory, it is possible that a base speeds up the reaction by reacting with the hydrogen chloride formed when the chlorine is removed from the ring by attack of the hydrogen. In the absence of a base, the hydrogen chloride produced tends to poison the palladium catalyst. This diminishes the activity of the catalyst, and leads to incomplete conversion of starting material to product.

It is well known that the chlorine group in the starting material is reactive toward nucleophiles. Accordingly, bases which are nucleophilic, such as the hydroxide ion, are to be avoided since such bases can readily attack the labile 4-chloro group and lead to the formation of undesirable products. Suitable bases include inorganic bases that are relatively insoluble in the chosen solvent, such as alkali and alkaline earth carbonates and bicarbonates. In addition, the alkali metal salts of low molecular weight carboxylic acids are particularly useful as bases. The low molecular weight carboxylic acids that are useful in this invention are the aliphatic acids containing two to six carbon atoms. While acids containing more than six carbons may serve as bases in the process, they tend to create problems of various sorts. For example, the salts of long chain acids containing 12 to 18 carbons can act as soaps and lead to foaming. In addition, hydrochloric acid is released during the reaction and this acid reacts with the sodium carboxylate to release the free carboxylic acid. Free carboxylic acid with more than six carbons can interfere in the workup of the product. Salts of formic acid are not desirable as the base because the presence of formate may lead to side reactions. These side reactions are illustrated in Comparative Examples 1 to 4 wherein formate is used as a reducing agent. When formate is used as a base, the chloro group is not fully removed. This is illustrated by Comparative Example 8 wherein formate is used as a base with hydrogen as a reducing agent. Alkali and alkaline earth carbonates and bicarbonates provide less catalytic effect than the carboxylate salts, although they do provide good yields. This is illustrated by Example 4, which shows that the reaction requires higher temperatures and is slower when carbonate is used as a base. The preferred base is sodium acetate.

The palladium catalyst can be used as a coating on any inert carrier. Barium sulfate is a suitable carrier. The preferred form for the catalyst is 5 to 10% coating on carbon.

The 3,5-diamino benzotrifluoride can be readily isolated and purified by methods such as solvent evaporation and recrystallization and other methods well known to those skilled in the art.

EXAMPLES

EXAMPLE 1

A solution of 4-chloro-3,5-dinitrobenzotrifluoride (DTI) (5.41g, 0.02 mol) in ethyl acetate (40 mL) was charged in a Parr hydrogenator bottle and mixed with sodium acetate (1.64g, 0.02 mol), and 5% Pd/C (0.5g). After purging with nitrogen, hydrogen was charged periodically in the reaction bottle to maintain its pressure at 50 psig. The temperature inside the reactor was maintained at 40° C. for 4 hours. After this duration, analysis of the reaction mixture by gas chromatography showed formation of 62.4% 3,5-diaminobenzotrifluoride (DABTF) and 34.9% 4-chloro-3,5-diaminobenzotrifluoride (CDABTF).

EXAMPLE 2

A solution of 4-chloro-3,5-dinitrobenzotrifluoride (DTI) (5.41g, 0.02 mol) in ethyl acetate (40 mL) was charged in a Parr hydrogenator bottle and mixed with sodium acetate (1.64g, 0.02 mol), and 5% Pd/C (0.5g). After purging with nitrogen, hydrogen was charged periodically in the reaction bottle to maintain its pressure at 50 psig. The temperature inside the reactor was maintained at 100° C. for 1.2 hours. After this duration, analysis of the reaction mixture by gas chromatography showed formation of 86.2% 3,5-diaminobenzotrifluoride (DABTF).

EXAMPLE 3

A solution of 4-chloro-3,5-dinitrobenzotrifluoride (DTI) (5.41g, 0.02 mol) in ethyl acetate (40 mL) was charged in a Parr hydrogenator bottle and mixed with sodium acetate (2.46g, 0.03 mol), and 5% Pd/C (0.5g). After purging with nitrogen, hydrogen was charged periodically in the reaction bottle to maintain its pressure at 50 psig. The temperature inside the reactor was maintained at 100° C. for 1 hours. After this duration, analysis of the reaction mixture by gas chromatography showed formation of 94.9% 3,5-diaminobenzotrifluoride (DABTF) and 1.3% 4-chloro-3,5-diaminobenzotrifluoride (CDABTF).

EXAMPLE 4

The reaction of Example 3 was repeated except that anhydrous sodium carbonate (3.18g, 0.03 mol) was used instead of sodium acetate. After heating the reaction mixture for 1 hour at 100° C., analysis of the reaction mixture by gas chromatography showed formation of 89.8% 3,5-diaminobenzotrifluoride (DABTF) and 7.2% 4-chloro-3,5-diaminobenzotrifluoride (CDABTF).

COMPARATIVE EXAMPLES

Comparative Example 1

A mixture of 4-chloro-3,5-dinitrobenzotrifluoride (1.0g, 0.0037 mol), sodium formate (2.1g, 0.0309 mol) and 10% palladium on carbon (Pd/C) (0.1g) were stirred in 10 mL of dimethyl formamide (DMF) and heated to 50.C. After 1 hour, analysis by Gas Chromatograph Mass Spectroscopy (GCMS) showed the formation of phenolic types of material, such as 3,5-dinitro-4-hydroxybenzotrifluoride and 3-amino-4-hydroxy-5-nitrobenzotrifluoride. No 3,5-diaminobenzotrifluoride (DABTF) was detected.

Comparative Example 2

A mixture of 4-chloro-3,5-dinitrobenzotrifluoride (1.0g, 0.0037 mol), sodium formate (2.49g, 0.0309 mol) and 10% Pd/C (0.1 g) were stirred in 10 mL of N-methyl-pyrrolidone (NMP) and heated to 115.C. After 1 hour, analysis by $^{19}F$ NMR indicated 3-amino-4-hydroxy-5-nitrobenzotrifluoride as the only fluorinated material formed.

Comparative Example 3

A mixture of 4-chloro-3,5-dinitrobenzotrifluoride (1.0g, 0.0037 mol), sodium formate (2.53g) and 10% Pd/C (0.1g) were stirred in 10 mL of dimethyl sulfoxide (DMSO) and heated to 115° C. After 1 hour, analysis by $^{19}F$ NMR indicated 3-amino-4-hydroxy-5-nitrobenzotrifluoride as the only fluorinated material.

Comparative Example 4

A mixture of 4-chloro-3,5-dinitrobenzotrifluoride (1.0g, 0.0037 mol), sodium formate (2.08g, 0.0306 mol) and 10% Pd/C (0.1g) were stirred in 10 mL of methanol and heated to 70° C. After 1 hour, analysis by GCMS indicated 3,5-dinitro-4-methoxybenzotrifluoride as the only fluorinated material.

Comparative Example 5

A solution of 4-chloro-3,5-dinitrobenzotrifluoride (15.0g) in isopropanol (150 mL) was charged in a Parr hydrogenator bottle and mixed with 1.5g of carbon supported palladium catalyst (5% Pd/C). After purging with nitrogen, hydrogen was charged periodically in the reaction bottle to maintain its pressure at 50 psig. The reaction temperature in the hydrogenator was kept at 45-100° C for 1 hour and then at 100° C. for 2.5 hours. After this duration, the analysis of the reaction mixture by gas chromatography showed formation of 38.5% 3,5-diaminobenzotrifluoride (DABTF) and 59.5% 4-chloro-3,5-diaminobenzotrifluoride (CDABTF).

75 mL of the reaction mixture from the end of the run was filtered to remove the catalyst. This was charged in the Parr hydrogenator reaction bottle and mixed with 0.75g of fresh Pd/C catalyst. The reduction reaction with hydrogen was carried out at 100° C. and 50 psig and after 4 hours the product analysis by gas chromatography showed 65.5% DABTF and 29.8% CDABTF.

Comparative Example 6

A solution of 4-chloro-3,5-dinitrobenzotrifluoride (15.0g) in isopropanol (150 mL) was charged in a 300 mL size autoclave and mixed with 1.5g of carbon supported palladium catalyst (5% Pd/C). After purging with nitrogen, hydrogen was charged periodically into the autoclave to maintain its pressure at 100 psig while it was heating to 150° C. during the initial ½ hour. The pressure was then increased to 150 psig with a continuous supply of hydrogen from a cylinder and the reaction temperature was maintained at 150° C. by a temperature controller. After 6 hours, the analysis of the reaction mixture by gas chromatography showed formation of 55.3% 3,5-diaminobenzotrifluoride (DABTF) and 6.3% 4-chloro-3,5-diaminobenzotrifluoride (CDABTF) and 27.1% of a lighter component which could be associated with the degradation of the solvent.

Comparative Example 7

A solution of 4-chloro-3,5-dinitrobenzotrifluoride (5.0g) in isopropanol (50 mL) was charged in a Parr hydrogenator bottle and mixed with 0.5g of carbon supported palladium catalyst (5% Pd/C). After purging with nitrogen, hydrogen was charged periodically in the reaction bottle to maintain its pressure at 50 psig. The reaction temperature in the hydrogenator was kept at 50° C. for 4.5 hours and then at 75° C. for 2 hours. After this duration, the analysis of the reaction mixture by gas chromatography showed formation of 23.7% 3,5-diaminobenzotrifluoride (DABTF) and 73.3% 4-chloro-3,5-diaminobenzotrifluoride (CDABTF).

Comparative Example 8

A solution of 4-chlor-3,5-dinitrobenzotrifluoride (DTI, 5.0 g, 0.02 mol) in ethyl acetate (50 mL) was charged in a Parr hydrogenator bottle and mixed with sodium formate (1.26 g, 0.02 mol) and 5% Pd/C (0.5 g). After purging with nitrogen, hydrogen was charged periodically in the reaction bottle to maintain its pressure at 50 psig. The temperature inside the reactor was maintained at 40° C. for 4 hours. After this duration, analysis of a sample of the reaction mixture contained only 44.4% 3,5-diaminobenzotrifluoride and 49.1% 4-chloro-3,5-diaminobenzotrifluoride. The run was continued another 8 hours. The composition was essentially unchanged.

We claim:

1. A process for the preparation of 3,5-diaminobenzotrifluoride which comprises treating 4-chloro-3,5-dinitrobenzotrifluoride, in a solvent selected from the group consisting of C-3 to C-6 secondary and tertiary alcohols, acetonitrile, low molecular weight esters of C-2 of C-4 alcohols and C-2 to C-4 acids, diethyl ether, tetrahydrofuran, ethylene glycol dimethyl ether, diethylene glycol dimethyl ether, triethylene glycol dimethyl ether, and tetraethylene glycol dimethyl ether, with hydrogen gas under a pressure of about 50 to 300 psi, in the presence of a suitable catalyst which comprises palladium on an inert carrier, and in the presence of a base selected from the group consisting of alkali metal and alkaline earth metal carbonates and bicarbonates, and alkali metal salts of C-2 to C-6 aliphatic carboxylic acids.

2. A process according to claim 1 in which the solvent is selected from the group consisting of C-3 to C-6 secondary and tertiary alcohols.

3. A process according to claim 2 in which the catalyst is palladium on carbon.

4. A process according to claim 3 in which the solvent is isopropyl alcohol.

5. A process according to claim 4 in which the base is sodium carbonate.

6. A process according to claim 4 in which the base is sodium acetate.

7. A process according to claim 1 in which the solvent is an ether.

8. A process according to claim 7 in which the base is sodium carbonate.

9. A process according to claim 7 in which the base is sodium acetate.

10. A process according to claim 1 in which the solvent is a low molecular weight ester.

11. A process according to claim 10 in which the base is sodium carbonate.

12. A process according to claim 10 in which the base is sodium acetate.

13. A process according to claim 1 in which the solvent is ethyl acetate.

14. A process according to claim 13 in which the catalyst is palladium on carbon.

15. A process according to claim 14 in which the base is sodium carbonate.

16. A process according to claim 14 in which the base is sodium acetate.

17. A process for the preparation of 3,5-diaminobenzotrifluoride which comprises
   (1) preparing a mixture consisting essentially of
      (a) 4-chloro-3,5-dinitrobenzotrifluoride;
      (b) a solvent selected from the group consisting of C-3 to C-6 secondary and tertiary alcohols, acetonitrile, low molecular weight esters of C-2 to C-4 alcohols and C-2 to C-4 acids, diethyl ether, tetrahydrofuran, ethylene glycol dimethyl ether, diethylene glycol dimethyl ether, triethylene glycol dimethyl ether, and tetraethylene glycol dimethyl ether;
      (c) hydrogen gas under a pressure of about 50 to about 300 psi;
      (d) a palladium catalyst; and
      (e) a base selected from the group consisting of alkali metal and alkaline earth metal carbonates and bicarbonates, and alkali metal salts of C-2 to C-6 aliphatic carboxylic acids; and
   (2) maintaining the temperature of said mixture to a temperature between room temperature and about 100° C.

18. A process according to claim 17 wherein said solvent is ethyl acetate.

19. A process according to claim 17 wherein said base is sodium carbonate.

20. A process according to claim 17 wherein said base is sodium acetate.

* * * * *